United States Patent [19]

Burzynski

[11] Patent Number: 5,116,622
[45] Date of Patent: May 26, 1992

[54] METHODS FOR TREATING PARKINSON'S DISEASE

[76] Inventor: Stanislaw R. Burzynski, 20 West Rivercrest, Houston, Tex. 77042

[21] Appl. No.: 581,022

[22] Filed: Sep. 12, 1990

[51] Int. Cl.$^5$ .............................................. A61K 35/22
[52] U.S. Cl. ...................................... 424/545; 514/2; 514/21; 514/328
[58] Field of Search ...................... 424/545; 514/2, 21, 514/328; 530/300, 344, 834

[56] References Cited

U.S. PATENT DOCUMENTS 4,470,970  9/1984  Burzynski .......................... 530/300
4,705,796  11/1987  Hendry et al. ....................... 514/328

Primary Examiner—Douglas W. Robinson
Assistant Examiner—Jean C. Witz
Attorney, Agent, or Firm—Arnold, White & Durkee

[57] ABSTRACT

The present invention provides methods for treating Parkinson's disease by administering to an afflicted host pharmaceutical compositions containing a therapeutically effective amount of urine peptide fractions containing 3-[N-phenylacetylaminopiperidine]-2,6-dion. The therapeutically effective urine peptide fractions of this invention, termed Antineoplastons A2 and A5, are obtained by two separate processes:

Antineoplaston A2 is prepared by
 providing a volume of urine;
 separating from the urine particulate matter and matter having a molecular weight greater than about 5000;
 acidifying the urine;
 separating from the acidified urine any precipitated matter;
 introducing the acidified urine to a first chromatography column containing a polymeric resin adsorbent;
 eluting the column to recover an eluate;
 adjusting the pH of the eluate to between about 2 and 8;
 introducing the adjusted eluate to a second chromatography column; and
 recovering the peptide fraction containing the compound 3-[N-phenylacetylaminopiperidine[-2,6-dion.

Antineoplaston A5 is prepared by
 providing a volume of urine;
 separating from the urine particulate matter and matter having a molecular weight greater than about 5000;
 acidifying the urine;
 separating from the acidified urine any precipitated matter;
 introducing the acidified urine to a chromatography column;
 eluting the column with a lower alkyl alcohol having from 1 to 8 carbon atoms; and
 recovering the peptide fraction containing the compound 3-[N-phenylacetylaminopiperidine]-2,6-dion.

6 Claims, No Drawings

METHODS FOR TREATING PARKINSON'S DISEASE

FIELD OF THE INVENTION

The present invention relates to methods of treating of neurological disorders, particularly Parkinson's disease.

BACKGROUND OF THE INVENTION

Parkinson's disease is a neurological disorder characterized by a decrease of voluntary movements. The afflicted patient has reduction of motor activity and slower voluntary movements compared to the normal individual. He has characteristic "mask" face, a tendency to hurry while walking, bent over posture and generalized weakness of the muscles. There is a typical "leadpipe" rigidity of passive movements. Another important feature of the disease is the tremor of the extremities occurring at rest and decreasing during movements.

Parkinson's disease, the etiology of which is unknown, belongs to a group of the most common movement disorders named parkinsonism, which affects approximately one person per one thousand. These other disorders grouped under the name of parkinsonism may result from viral infection, syphilis, arteriosclerosis and trauma and exposure to toxic chemicals and narcotics.

Regardless of the cause of the disease, the main pathologic feature is degeneration of dopaminergic cells in basal ganglia, especially in substantia nigra. Due to premature death of the dopamine containing neurons in substantia nigra, the largest structure of the basal ganglia, the striatum, will have reduced input from substantia nigra resulting in decreased dopamine release. The understanding of the underlying pathology led to the introduction of the first successful treatment which can alleviate Parkinson's disease. Virtually all approaches to the therapy of the disease are based on dopamine replacement. Drugs currently used in the treatment can be converted into dopamine after crossing the blood brain barrier, or they can boost the synthesis of dopamine and reduce its breakdown. Unfortunately, the main pathologic event, degeneration of the cells in substantia nigra, is not helped. The disease continues to progress and frequently after a certain length of time, dopamine replacement treatment will lose its effectiveness.

The treatment representing this invention is based on a different principle: the reducing of degeneration of the cells and promoting healing in substantia nigra.

The human body has remarkable potential for regeneration. When the body incurs damage to the tissue, there is an immediate rise of new cells which replace those that were damaged. Unfortunately, in the adult human brain, the dead neurons are not replaced. The basic dogma in neuroscience is that once the adult set of neurons has been produced, no stem cells persist to generate new neurons. Such rule applied for both vertebrates and invertebrates. Recent studies of Nottebohm et al. seem to challenge this dogma by proving that the occurrence of new neurons can continue in the brain of the adult bird (Alvarez-Buylla and Nottebohm, *Nature*, 335:353 (1988)). During the development, the cells are undergoing a process of differentiation. After they reach terminal differentiation, they will remain viable for a long time, but they won't be able to proliferate. In order to survive, these cells will need a continuous supply of growth factors (Seshadri and Campisi, *Science*, 247:205 (1990)). The availability of certain growth factors will determine whether neurons will live shorter or longer lives. Nerve growth factor is the best characterized polypeptide growth factor in the nervous system (Levi-Montalcini and Angeletti, *Physiol. Rev.*, 48:534 (1968)). Recently, the additional polypeptide growth factors active in the nervous system have been described: brain-derived neurotrophic factor and neurotrophin-3 (Leibrock et al., *Nature*, 341:149 (1989); Maisonpierre et al., *Science*, 247:1446 (1990)). It has been postulated that these polypeptide factors can be used in overcoming neuronal degeneration, but they have not been used as yet with success in the treatment of Parkinson's disease.

Antineoplastons are differentiation inducing peptides and amino acid derivatives, which were first described by S. R. Burzynski (Burzynski, U.S. Pat. No. 4,470,970; Burzynski, *Drugs Exptl. Clin. Res. Suppl.* 1, 12:1 (1986)). Interestingly, Antineoplastons inhibit neoplastic growth, and at the same time stimulate normal cell growth (Burzynski, *Physiol. Chem. Phys.*, 8:275 (1976)). During clinical applications, Antineoplastons A2 and A5 have shown prominent stimulation of the growth of the cells of ectodermal origin, such as epidermis (Burzynski, *Drugs Exptl. Clin. Res. Suppl.* 1, 13:1 (1987) and 13:1, 37 (1987)). In the human body, the nervous system develops from the cells of the neural tube and the neural crest, which originate from the ectoderm. Initial observation of the stimulatory effect of Antineoplastons on the cells from ectodermal origin helped to introduce the hypothesis that Antineoplastons may also have a stimulatory effect on the cells of the central nervous system, which will extend survival of these cells. The increased survival of the cells in substantia nigra may improve the symptoms of Parkinson's disease and possibly arrest the progression of the disease.

SUMMARY OF THE INVENTION

Antineoplastons A2 and A5 are administered for the purpose of the treatment of Parkinson's disease. Concentrations of both formulations used for the treatment range from about 1 to about 40 mg total solids/ml, a preferred dose being 25 mg total solids/ml.

Antineoplastons A2 and A5 are designations of a specific urine peptide fraction containing the compound 3-[N-phenylacetylaminopiperidine]-2,6-dion. The processes for obtaining Antineoplastons A2 and A5 are described in detail in U.S. Pat. No. 4,470,970, the entire text of which is hereby incorporated by reference. Briefly, Antineoplaston A2 is a urine peptide fraction containing the compound 3-[N-phenylacetylaminopiperidine]-2,6-dion prepared by providing a volume of urine;

separating from the urine particulate matter and matter having a molecular weight greater than about 5000;

acidifying the urine;

separating from the acidified urine any precipitated matter;

introducing the acidified urine to a first chromatography column containing a polymeric resin adsorbent;

eluting the column to recover an eluate;

adjusting the pH of the eluate to between about 2 and 8;

introducing the adjusted eluate to a second chromatography column; and recovering the peptide fraction containing the compound 3-[N-phenylacetylaminopiperidine]-2,6-dion.

Antineoplaston A5 is a urine peptide fraction containing the compound 3-[N-phenylacetylaminopiperidine]-2,6-dion prepared by providing a volume of urine;

separating from the urine particulate matter and matter having a molecular weight greater than about 5000;

separating from the acidified urine any precipitated matter;

introducing the acidified urine to a chromatography column;

eluting the column with a lower alkyl alcohol having from 1 to 8 carbon atoms; and recovering the peptide fraction containing the compound 3-[N-phenylacetylaminopiperidine]-2,6-dion.

Previously, in Hendry et al., U.S. Pat. No. 4,705,796, 3-[N-phenylacetylaminopiperidine]-2,6-dion was described as useful for treating neuropsychiatric disorders, including Parkinson's disease. Unexpectedly, the present inventor has found that urine peptide fractions Antineoplaston A2 and Antineoplaston A5 provide a surprisingly better degree of therapeutic effectiveness than the synthetically prepared 3-[N-phenylacetylaminopiperidine]-2,6-dion. Evidently, the urine peptide fractions of Antineoplaston A2 and Antineoplaston A5 contain additional peptides or urine components which exert additional and independent therapeutic activity in treating Parkinson's disease.

While not wishing to be limited by a proposed mechanism of action, the present inventor believes that the mechanism of action of Antineoplastons A2 and A5 in the treatment of Parkinson's disease is completely different from the mechanism of action of 3-[N-phenylacetylaminopiperidine]-2,6-dion (herein referred to as Antineoplaston A10). The key part in maintaining neurons of substantia nigra is attributed to astrocytes (Ransom, *The Biochemical Pathology of Astrocytes*, Allan R. Liss, Eds., 203 (1988)). Astrocytes are producing growth factors which are necessary for prevention of degeneration of the neurons. In the patient who has Parkinson's disease, astrocytes are unable to produce a sufficient amount of growth factors because of errors in DNA program for production of these factors. This results in degeneration and death of neurons and later astrocytes. Antineoplastons A2 and A5 are believed to "reprogram" defective astrocytes, which will result in the production of a sufficient amount of growth factors necessary for maintenance of neurons in substantia nigra.

Antineoplaston A10 is a weak inhibitor of monoamine oxidase-B (MAO-B), and as such, may help patients who have parkinsonism produced by toxic chemicals, such as MPTP. MPTP, which is present as impurity in "designer drugs," enters astrocytes where it is converted by MAO-B to $MPP^+$. $MPP^-$, which is the actual neurotoxin, is transported to nearby neurons, and is ultimately responsible for neuronal death (Snyder and D'Amato, *Neurology*, 36:250 (1986)). Antineoplaston A10 may help under such circumstances by inhibiting MAO-B and reducing conversion of MPTP to $MPP^+$.

Unfortunately, in original Parkinson's disease which is not caused by exposure to toxic chemicals, Antineoplaston A10 does not have practical application. Patients with original Parkinson's disease receiving treatment with Antineoplaston A10 did not show any improvement.

DETAILED DESCRIPTION OF THE PREFERRED EMBODIMENTS

As stated above, urine peptide fractions termed Antineoplastons A2 and A5 are useful in the treatment of Parkinson's disease. Pharmaceutical compositions containing Antineoplaston A2 or A5 can be prepared as described below.

The dried solids of the urine peptide fractions Antineoplaston A2 or A5 are included in the pharmaceutically acceptable carrier or diluent in an amount sufficient to exert a therapeutic effect. The urine peptide fractions can be administered by any appropriate route, for example, orally, parenterally, intravenously, intradermally, subcutaneously or intraperitoneally, in liquid or solid form.

The urine peptide fraction is included in the pharmaceutically acceptable carrier in an amount sufficient to exert a therapeutically useful effect on the Parkinson's diseased patient without serious toxic effect. The amount of Antineoplaston A2 or A5 administered to a patient will depend upon absorption, inactivation and excretion rates of the active ingredient, as well as other factors known to those skilled in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The active ingredient may be administered at once, or may be divided into a number of smaller doses to be administered at varying intervals of time. The dosage of the active compounds sufficient to produce a therapeutic effect in Parkinson's disease is generally 14 mg/kg/day-100 mg/kg/day, preferably 40 mg/kg/day. In the case of humans, an amount of about 1 g-7 g/day, preferably about 3 g/day, is administered in 1-4 divided doses daily, or as a sustained release form.

If oral administration is desired, although not required, the Antineoplaston A2 or A5 composition may be provided in a form that protects it from the acidic environment of the stomach. The Antineoplastons can be orally administered in combination with an antacid formulation. The composition can also be administered in an enteric coating that maintains its integrity in the stomach and releases the active compound in the intestine.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, capsules, elixirs, suspensions, syrups or the like. Pharmaceutically compatible binding agents and/or adjuvant materials can be included as part of the composition.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are 5% dextrose, sterile water for injection, physiological saline or phosphate buffered saline (PBS).

EXAMPLE 1

(Patient: R.B.)

When initially seen by me in October 1987, the patient was a 54-year-old white male who complained of generalized muscle weakness, stiffness, tremor of the extremities, difficulty in walking and posture changes. In addition, he had shortness of breath, dizziness, and the presence of enlarged lymph nodes on both sides of the neck, axillary areas and both inguinal areas.

This patient was in reasonable health until 1984 when he was diagnosed with Parkinson's disease and began treatment with Sinemet and Parlodel. In November 1986, he found a nodule in his right groin. The biopsy of the nodule showed "Follicular hyperplasia." However, during the following months, he developed a number of new nodules and the revised pathology report confirmed diagnosis of "Nodular, poorly differentiated lymphocytic lymphoma." The disease was further progressing and the patient developed enlargement of the spleen, a tumor in the abdomen and the involvement of bone marrow by malignant lymphoma. On Oct. 22, 1987, the patient began the treatment under my care for "Nodular, poorly differentiated lymphocytic lymphoma, stage IV" and was treated with Antineoplaston A10 (synthetically produced 3-[N-phenylacetylaminopiperidine]-2,6-dion) and AS2-1 (1:4 ratio of sodium salts of phenylacetylglutamine and phenylacetic acid) 500 mg capsules. Periodically, the treatment was also combined with low dose Cytoxan. The treatment resulted in partial remission of malignant lymphoma. However, there was no improvement in the symptoms and signs of Parkinson's disease.

On Jan. 23, 1990, the patient began the treatment with Antineoplaston A5 intravenous injections aimed at improvement of Parkinson's disease. The dose of the formulation was gradually increased to 1 g IV three times daily. According to the evaluation of Apr. 3, 1990, the patient had marked reduction of the symptoms and signs of Parkinson's disease. The follow-up examination of May 15, 1990 revealed further improvement. The patient noted that his arms were no longer "lifeless". He was able to walk easier than before. The evaluation on Aug. 2, 1990 revealed further improvement in fine movements of the upper extremities. Previously, the patient had great difficulty in dressing himself, in buttoning his shirt and writing. The examination of Aug. 2, 1990 revealed that he could perform these tasks with more ease. The patient continues the treatment at present.

EXAMPLE 2

(Patient: M.D.)

When coming under my care for the treatment of Parkinson's disease, this patient was a 42-year-old white male who complained of tremor of the upper left extremity (aggravating at rest), stiffness of the upper left extremity, slowness in movement and reduced expression of the face ("mask" face). He was diagnosed with Parkinson's disease three years before coming under my care and was treated with Sinemet, which allowed him to have some improvement. The patient began the treatment with Antineoplaston A5, 25 mg/ml injections on Oct. 3, 1989. The dosage of the formulation was gradually increased to 0.75 g IV three times daily. On Dec. 7, 1989, Antineoplaston A2, 25 mg/ml injections were added to the treatment. The dosage of this formulation was gradually increased to 0.375 g IV three times daily. As noticed on Oct. 18, 1989, the patient had less tremor of the upper left extremity. He had further reduction of tremor as documented on Nov. 1, 1989. On Nov. 10, 1989, a physical examination revealed the patient experienced less muscle stiffness. After the addition of Antineoplaston A2 on Jan. 9, 1990, he has shown more activity of the face muscles.

What is claimed is:

1. A method of treating original Parkrinson's disease in an afflicted host comprising:
    administering to the host a pharmaceutical composition containing a therapeutically effective amount of a urine peptide fraction containing 3-[N-phenylacetylaminopiperidine]-2,6-dion, the urine peptide fraction obtained by
    providing a volume of urine;
    separating from the urine particulate matter and matter having a molecular weight greater than about 5000;
    acidifying the urine;
    separating from the acidified urine any precipitated matter;
    introducing the acidified urine to a first chromatography column containing a polymeric resin adsorbent;
    eluting the column to recover an eluate;
    adjusting the pH of the eluate to between about 2 and 8;
    introducing the adjusted eluate to a second chromatography column; and
    recovering the peptide fraction containing the compound 3-[N-phenylacetylaminopiperidine]-2,6-dion.

2. The method of claim I wherein the active compound is administered orally or by injection.

3. The method of claim 1 wherein the urine peptide fraction is administered to humans in the amount of 1-7 g/day.

4. A method of treating original Parkinson's disease in an afflicted host comprising:
    administering to the host a pharmaceutical composition containing a therapeutically effective amount of a urine peptide fraction containing 3-[N-phenylacetylaminopiperidine]-2,6-dion, the urine peptide fraction obtained by
    providing a volume of urine;
    separating from the urine particulate matter and matter having a molecular weight greater than about 5000;
    acidifying the urine;
    separating from the acidified urine any precipitated matter;
    introducing the acidified urine to a chromatography column;
    eluting the column with a lower alkyl alcohol having from 1 to 8 carbon atoms; and
    recovering the peptide fraction containing the compound 3-[N-phenylacetylaminopiperidine]-2,6-dion.

5. The method of claim 4 wherein the active compound is administered orally or by injection.

6. The method of claim 4 wherein the active compound is administered to humans in the amount of 1-7 g/day.

* * * * *

UNITED STATES PATENT AND TRADEMARK OFFICE
CERTIFICATE OF CORRECTION

PATENT NO. : 5,116,622
DATED : May 26, 1992
INVENTOR(S) : Stanislaw R. Burzynski It is certified that error appears in the above-indentified patent and that said Letters Patent is hereby corrected as shown below:

Column 6, line 14, "Parkrinson's" should read -- Parkinson's--.

Signed and Sealed this

Seventeenth Day of August, 1993

*Attest:*

BRUCE LEHMAN

*Attesting Officer*  *Commissioner of Patents and Trademarks*